United States Patent [19]

Albers-Schonberg et al.

[11] 4,385,065

[45] May 24, 1983

[54] NOVEL SUBSTANCES AND PROCESS FOR THEIR PRODUCTION

[75] Inventors: George E. Albers-Schonberg, Princeton, N.J.; Sebastian Hernandez, Madrid, Spain; Leeyuan Huang, Westfield, N.J.

[73] Assignee: Merck & Co., Inc., Rahway, N.J.

[21] Appl. No.: 308,294

[22] Filed: Oct. 5, 1981

Related U.S. Application Data

[63] Continuation-in-part of Ser. No. 199,900, Oct. 23, 1980, abandoned.

[51] Int. Cl.$^3$ .................. C07D 313/00; A61K 31/365
[52] U.S. Cl. .................................... 424/279; 549/266; 435/124
[58] Field of Search ................ 260/343; 424/180, 279; 536/1, 4; 549/266

[56] References Cited

FOREIGN PATENT DOCUMENTS 1573955  8/1980  United Kingdom .

OTHER PUBLICATIONS

Huang et al., Abstract from 20th Interscience Conf. on Antimicrobial Agents & Chemotherapy (9/80).

Primary Examiner—Jane T. Fan
Attorney, Agent, or Firm—David L. Rose; Mario A. Monaco

[57] ABSTRACT

There is disclosed a novel series of compounds isolated from the fermentation broth of a strain of the microorganism Streptomyces sp MA5038. The compounds have a 16-membered macrocyclic lactone structure with various substituents thereon. The compounds have insecticidal and antitapeworm activity and compositions for such uses are disclosed.

10 Claims, No Drawings

NOVEL SUBSTANCES AND PROCESS FOR THEIR PRODUCTION

CROSS REFERENCE TO RELATED APPLICATIONS

This application is a continuation-in-part of our copending application Ser. No. 199,900 filed Oct. 23, 1980 now abandoned.

SUMMARY OF THE INVENTION

This invention is concerned with novel chemical compounds. In particular, it is concerned with novel macrocyclic lactones which are produced by the fermentation of a nutrient medium with a strain of the microorganism Streptomyces Sp. Ma-5038. Thus, it is an object of this invention to provide for novel compounds, and a method for preparing such products microbiologically. It is a further object of this invention to provide for a method for the recovery and purification of such compounds from the fermentation broth. These substances have insecticidal activity, in particular antitapeworm activity, and it is, thus, an additional object of this invention to provide novel insecticidal and antitapeworm compositions containing one or more of the disclosed compounds. Further objects of this invention will become apparent from the following description of this invention.

DESCRIPTION OF THE INVENTION

In accordance with this invention, a class of substances is described, which is prepared by growing under controlled conditions, a previously undescribed strain of microorganism. At least three distinct but closely related novel compounds are produced by Streptomyces Sp. MA-5038. They are referred to herein as $A_1$, $A_2$ and $B_1$. Compound $A_1$ is the major component, produced in the greatest quantity. Compounds $A_2$ and $B_1$ are minor components of the isolated material. They are obtained by fermentation and recovered in substantially pure form as described herein.

Based on taxonomic studies, the microorganisms capable of producing these compounds are of a new species of the genus Streptomyces. One such culture, isolated from soil, is designated MA-5038 in the culture collection of Merck & Co., Inc., Rahway, New Jersey. A sample of this culture, capable of producing the herein described compounds, has been deposited, without restriction as to availability, in the permanent culture collection of the American Type Culture Collection at 12301 Parklawn Drive, Rockville, Maryland 20852, and has been assigned the concession number ATCC 31587.

The morphological and cultural characteristics of Streptomyces sp. MA-5038 are set forth below:

CULTURAL CHARACTERISTICS OF:

Streptomyces sp. MA-5038-ATCC 31587

(V = vegetative growth; A = aerial mycelium; SP = soluble pigment)

Morphology: Sporophores are produced at terminal portions of branching hyphae. Sporophores are in chains of more than 10 spores, forming loops, loose coils and loose spirals. Spores are spherical to oval or cylindrical, $0.9\mu \times 1.2\mu$ (950X). Spore surface is smooth (electron microscopy).

Oatmeal agar (ISP Medium 3)
 V: Brown edged with yellow-tan
 A: Moderate, creamy white to pinkish cream (3ca)γ
 SP: None
Czapek Dox agar (sucrose nitrate agar)
 V: Tan
 A: Moderate, pale yellowish-pink (3ca)γ
 SP: Pink
Glycerol asparagine agar (ISP Medium 5)
 V: Cream to light tan
 A: Moderate, cream with pink cast
 SP: Pale yellowish-rose
Inorganic salts-starch agar (ISP Medium 4)
 V: Yellowish-tan
 A: Moderate, creamy white
 SP: None
Yeast extract-dextrose + salts agar
 V: Brown edged with light brown and yellow tan segments
 A: Moderate, creamy white with pink cast
 SP: None
Yeast extract-malt extract agar (ISP Medium 2)
 V: Brown edged with light brown and yellow-tan segments
 A: Moderate, creamy white to pale yellowish pink (3ca)γ
 SP: None
Peptone-iron-yeast extract agar
 V: Tan
 A: None
 SP: None
 Melanin: Negative
 $H_2S$ production: Negative
Nutrient starch agar
 V: Tan
 A: Sparse, whitish
 SP: None
 Hydrolysis of starch moderate
Nutrient gelatin agar
 V: Tan
 A: Sparse, whitish
 SP: None
 Liquefaction of gelatin moderate
Nutrient tyrosine agar
 V: Tan
 A: Sparse, whitish
 SP: Very slight browning of medium
 Decomposition of tyrosine: Moderate
Carbon utilization
 Pridham-Gottlieb basal medium + 1% carbon source; + = growth; ± = growth poor or questionable; − = no growth as compared to negative control (no carbon source).

| | |
|---|---|
| Glucose | + |
| Arabinose | + |
| Cellulose | − |
| Fructose | + |
| Inositol | + |
| Lactose | + |
| Maltose | + |
| Mannitol | + |
| Mannose | + |
| Raffinose | + |
| Rhamnose | + |
| Sucrose | + |
| Xylose | + |
| Temperature range: | (Yeast extract-dextrose + salts agar) |

28° C. - Good vegetative growth, moderate aerial

-continued growth and sporulation
37° C. - Good vegetative growth, no aerial growth
50° C. - No growth
Oxygen requirements (Stab culture in yeast extract-
dextrose + salts agar):
Aerobic
All readings taken after three weeks at 28° C. unless
noted otherwise. pH of all media approximately
neutral (6.8-7.2).

*Color number designations taken from Color Harmony Manual, 1958 4th Edision, Container Corporation of America, Chicago, Illinois.

A careful comparison of the foregoing data with published descriptions, including Bergey's Manual of Determinative Bacteriology (Eighth Edition) of known microorganisms reveals significant differences that the instant microorganisms should be classified as a new species. On this basis, it was designated Streptomyces sp. MA-5038.

The above description is illustrative of a strain of Streptomyces sp. MA-5038 which can be employed in the production of the instant compounds. However, the present invention also embraces mutants of the above described microorganism. For example, those mutants which are obtained by natural selection or those produced by mutating agents including ionizing radiation such as ultraviolet irradiation, or chemical mutagens such as nitrosoguanidine or the like treatments are also included within the ambit of this invention.

The instant compounds are produced during the aerobic fermentation of suitable aqueous nutrient media under conditions described hereinafter, with a producing strain of Streptomyces sp. MA-5038. Aqueous media such as those used for the production of many antibiotic substances are suitable for use in this process for the production of these macrocyclic compounds.

Such nutrient media containing sources of carbon and nitrogen assimilable by the microorganism and generally low levels of inorganic salts. In addition, the fermentation media may contain traces of metals necessary for the growth of the microorganisms, and production of the desired compounds. These are usually present in sufficient concentrations in the complex sources of carbon and nitrogen, which may be used as nutrient sources, but can, of course, be added separately to the medium if desired.

In general, carbohydrates such as sugars, for example dextrose, sucrose, maltose, lactose, dextran, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount of carbohydrate between 0.5 and 5% by weight of the medium is satisfactory. These carbon sources can be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, distillers solubles, cottonseed meal, meat extract and the like, are readily assimilable by Streptomyces sp. MA-5038 in the production of the instant compounds. The various sources of nitrogen can be used alone or in combination in amounts ranging from 0.2 to 6% by weight of the medium.

Among the nutrient inorganic salts, which can be incorporated in the culture media are the customary salts capable of yielding sodium, potassium, magnesium ammonium, calcium, phosphate, sulfate, chloride, carbonate, and like ions. Also included are trace metals such as cobalt, manganese, ions and the like.

It should be noted that the media described hereinbelow and in the Examples are merely illustrative of the wide variety of media, which may be employed, and are not intended to be limitative.

The following are Examples of media suitable for growing strains of Streptomyces sp. MA-5038.

| Medium A | |
|---|---|
| Dextrose | 1.0 g. |
| Soluble starch | 10.0 g. |
| Beef extract | 3.0 g. |
| Yeast autolysate | 5.0 g. |
| NZ Amine-E | 5.0 g. |
| MgSO$_4$.7H$_2$O | 0.05 g. |
| KH$_2$PO$_4$ | 0.182 g. |
| Na$_2$HPO$_4$ | 0.190 g. |
| CaCO$_3$ | 0.5 g. |
| Distilled water | 1000 ml. |
| pH 7.0-7.2 | |
| Medium B | |
| Tomato paste | 20.0 g. |
| Primary yeast | 10.0 g. |
| Dextrin (CPC starch) | 20.0 g. |
| CoCl$_2$.6H$_2$O | 0.005 g. |
| Distilled water | 1000 ml. |
| pH 7.2-7.4 | |
| Medium C | |
| Corn meal | 20.0 g. |
| Distillers solubles | 10.0 g. |
| Soybean meal | 15.0 g. |
| Sodium citrate | 4.0 g. |
| CaCl$_2$.2H$_2$O | 0.5 g. |
| MgSO$_4$.7H$_2$O | 0.1 g. |
| CoCl$_2$.6H$_2$O | 0.01 g. |
| FeSO$_4$.2H$_2$O | 0.01 g. |
| Polyglycol P2000 (Polypropylene glycol mw 2000) | 2.5 ml. |
| Distilled water | 1000 ml. |
| pH 6.5 | |
| Medium D | |
| Lactose | 20.0 g. |
| Distillers solubles | 15.0 g. |
| Autolyzed yeast (Ardamine pH) | 5.0 g. |
| Distilled water | q.s. to 1000 ml. |
| pH 7.0 | |
| Medium E | |
| Tomato paste | 40.0 g. |
| Oat flour | 10.0 g. |
| Distilled water | 1000 ml. |
| pH 7.0 | |

The fermentation employing Streptomyces sp. MA-5038 can be conducted at temperatures ranging from about 20° C. to about 40° C. For optimum results, it is most convenient to conduct these fermentations at a temperature in the range of from about 24° C. to about 30° C. Temperatures of about 27°-28° C. are most preferred. The pH of the nutrient medium suitable for producing the instant compounds can vary from about 5.0 to 9.0 with a preferred range of from about 6.0 to 7.5.

Small scale fermentations are conveniently carried out by placing suitable quantities of nutrient medium in a flask employing known sterile techniques, inoculating the flask with either spores or vegetative cellular growth of *Streptomyces sp.* MA-5038 loosely stoppering the flask with cotton and permitting the fermentation to proceed in a constant room temperature of about 28° C. on a rotary shaker for about 3 to 10 days. For larger scale work, it is preferable to conduct the fermentation in suitable tanks provided with an agitator and a means of aerating the fermentation medium. The nutrient medium is made up in the tank and after sterilization is inoculated with a suitable source of vegetative cellular growth of Streptomyces sp. MA-5038. The fermentation is allowed to continue for from 1 to 8 days while agitating and/or aerating the nutrient medium at a temperature in the range of from about 24° to 37° C. The degree of aeration is dependent upon several factors such as the size of the fermentor, agitation speed, and the like. Generally the larger scale fermentations are agitated at about 95 to 150 RPM and about 2 to 20 cubic feet per minute (CFM) of air.

The novel compounds of this invention are found primarily in the mycelium on termination of the Streptomyces sp. MA-5038 fermentation and may be removed and separated from one another as described below. The three major compounds are identified as $A_1$, $A_2$, and $B_1$. There are a considerable number of minor related components present in the broth which are at present unisolated and unidentified. The approximate ratio of the isolated major components is as follows: $A_1:A_2:B_1::10:1:4$. Components $A_1$ and $A_2$ are acidic components whose Rf in thin layer chromatography are dependent upon ammonia in the solvent system. The Rf of the $B_1$ component is not ammonia dependent in its thin layer chromatography analysis.

The separation of the novel compounds from the whole fermentation broth and the recovery of the individual compounds is carried out by solvent extraction and application of chromatographic fractionations with various chromatographic techniques and solvent systems.

The instant compounds have slight solubility in water, but are soluble in organic solvents. This property may be conveniently employed to recover the compounds from the fermentation broth. Thus, in one recovery method, the whole fermentation broth is combined with approximately an equal volume of an organic solvent. While any organic solvent may be employed, it is preferable to use a water miscible solvent such as acetone, methanol, ethanol and the like. Generally several extractions are desireable to achieve maximum recovery. The solvent removes the instant compounds as well as other substances lacking the antiparasitic activity of the instant compounds. If the solvent is a water miscible one, the solvent and water are combined into a single phase and filtered. The organic solvent is evaporated under reduced pressure and the remaining aqueous phase placed onto a chromatography column containing preferably, the highly cross-linked polystyrene resin, XAD-II (available from Rohm and Haas). The column retains the desired products and some impurities, but lets many of the impurities, particularly the water soluble impurities, pass through. The column is washed with water to further remove impurities, and is then washed with an organic solvent which acetone, methanol, and ethanol and the like are preferred organic solvents. The solvent is evaporated and the residue further chromatographed using column chromatography, thin layer chromatography, preparative layer chromatography, and the like, with silica gel, aluminum oxide, ion exchange resins, dextran gels and the like, as the chromatographic medium, with various solvents and combinations of solvents as the eluent. Thin layer and preparative layer chromatography may be employed to detect the presence of, and to isolate the individual compounds. The use of the foregoing techniques as well as others known to those skilled in the art, will afford purified compositions containing mixtures of the instant compounds as well as the individual compounds themselves. The presence of the desired compounds is determined by analyzing the various chromatographic fractions for biological activity or physico-chemical characteristics. The structures of the instant compounds have been determined by detailed analysis of the various spectral characteristics of the compounds, in particular their nuclear magnetic resonance, mass, ultraviolet and infrared spectra.

Based on these experimental data, the instant compounds are believed to have the following structural formula:

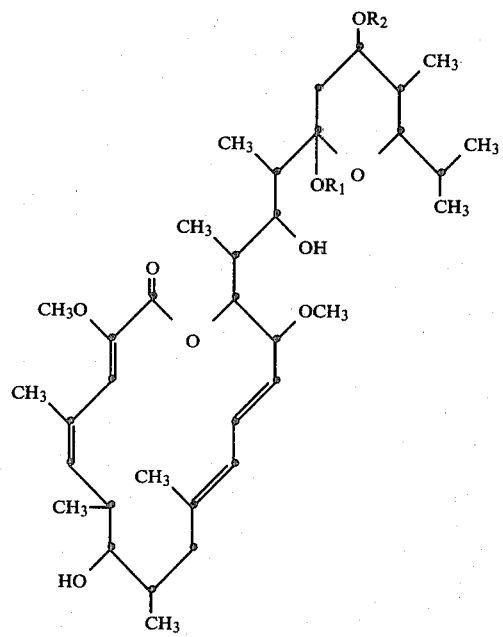

The variables $R_1$ and $R_2$ in the foregoing structure have the following definitions for the instant compounds:

| Compound | $R_1$ | $R_2$ |
|----------|-------|-------|
| $A_1$ | H | —CO—CH=CH—COOH |
| $A_2$ | —CH$_3$ | —CO—CH=CH—COOH |
| $B_1$ | H | CH$_3$ |

The novel compounds of this invention have significant parasiticidal activity as insecticides, and parasiticides. The compounds are of value against arthropods parasitizing man, biting insects and other dipterous pests causing annoyance to man.

The compounds are also active against household pests such as the cockroach, Blatella sp., clothes moth, Tineola sp., carpet beetle, Attagenus sp. and the housefly, Musca domestica.

The compounds are also useful against insect pests of stored grains such as Tribolium sp., Tenebrio sp. and of agricultural plants such as spider mites, (Tetranychus sp.), aphids, (Acyrthiosiphon migratory orthopterans such as locusts and immature stages of insects living on plant tissue.

The antiparasitic agents of this invention are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally, good results are obtained with our novel compounds by the application of the insect of a solution or suspension of from about containing from 5 to 50 parts per million of the active compounds. The compound may be applied at one time or in divided doses over a relatively short period of time such as 1-5 days. With the preferred compounds of the invention, excellent control of such parasites is obtained in animals by administering a solution or suspension containing from about 500 to 10,000 parts per million of the active compound in a single dose. Repeat treatments are given as required to combat reinfections and are dependent upon the species of parasite and the husbandry techniques being employed. The techniques for administering these materials to animals are known to those skilled in the veterinary field.

The compounds of this invention show activity against the earthworm nematode *Caenorhabditis elegans* at in vitro levels of less than 30 micrograms per ml. The compounds also very effectively stimulate the release of γ-amino butyric acid from isolated rate brain synaptosomes.

When the compounds described herein are administered, compositions are provided in which the active compound or compounds are intimately dispersed in an inert carrier or diluent. By inert carrier is meant one that will not react with the insecticidal agent and one that may be applied safely to the surface or area upon which the insect is found.

In using the compounds of this invention, the individual components may be isolated and purified and used in that form. Alternatively, mixtures of more than one of the individual components may be used. It is not necessary to completely separate the various compounds obtained from the purification of the fermentation broth. Generally, there is obtained a mixture containing two or more of the compounds, but having other unrelated compounds excluded therefrom, and such mixture may be used for the prevention and treatment of insect infestations as described herein. Such a mixture generally will contain unequal proportions of the compounds, however, all of the compounds have substantial activity and the insecticidal activity of the mixture can be accurately determined.

When the compounds of this invention are used in combatting agricultural pests that inflict damage upon crops while they are growing or while in storage, the compounds are applied using known techniques as sprays, dusts, emulsions and the like, to the growing or stored crops to effect protection from such agricultural pests.

The compounds are particularly active against tapeworms, a form of cestode parasite, which infect man and animals. The tapeworm is a common parasite which, although often symptomless, can lead to various gastrointestinal and other disorders. Tapeworms such as *Hymenolepis diminuta, Hymenolepis nana, Taenia seginata, Taenia solium* and *Diphyllobothrium latum* are commonly found in such infections.

When the compounds of this invention are administered for the treatment of tapeworms, oral administration is preferred.

The active compounds of the present invention when used to treat the above disorders, are orally administered, for example, with an inert diluent an organic solvent, or with an assimilable edible carrier, or they may be enclosed in hard or soft gelatin capsules, or they may be compressed into tablets, or they may be incorporated directly with the food of the diet. For oral therapeutic administration, the active compound of this invention may be incorporated with excipients and used in the form of tablets, troches, capsules, elixirs, suppositories, suspensions, syrups, wafers, chewing gum, and the like. The amount of active compound in such therapeutically useful compositions or preparations is such that a suitable dosage will be obtained.

The tablets, troches, pill, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type, a liquid carrier such as a fatty oil. Various other materials may be present as coatings or to otherwise modify the physical form of the dosage unit, for instance, tablets, pills or capsules may be coated with shellac, sugar or broth. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amount employed.

When used in the above formulation, the instant compound is employed at dosages sufficient to treat tapeworm infections. The dosages may be given a single daily dose or in divided dosages throughout the day. The specific dose given to a patient will vary with the severity of the condition, and the weight of the patient. As such, dosages of from about 1 to 25 mg/kg/day have been found to be effective. Such doses may be divided to provide for up to 4 administrations per day. Preferred doses are of from 2 to 10 mg/kg/day. The treatment may be carried out over several days to insure that the parasite is completely destroyed. Generally, treatment periods of from 1 to 21 days are adequate.

The following examples are being provided in order that the instant invention may be more fully understood. Such examples are not to be construed as being limitative of the invention.

EXAMPLE 1

A frozen vial of Streptomyces Sp. MA-5038 is used to inoculate 54 ml. of Medium A in a 250 ml. baffled Erlenmeyer flask. The flask is incubated at 28° C. for 1 day at 220 r.p.m. on a rotary shaking machine. The flask is then stored at 8° C. for 3 days before the contents are used to inoculate 44 ml. of Medium D using 5% inoculum in a −250 ml. unbaffled Erlenmeyer flasks. The flask is incubated for 4 days at 28° C. at 220 r.p.m. on a rotary shaking machine.

EXAMPLE 2

570 Ml. of the culture broth as prepared in Example 1 is extracted with 600 ml. of acetone and filtered through a bed of diatomaceous earth filtering aid. The acetone is removed from the aqueous mixture by evaporation in vacuo. The aqueous suspension is passed through a water equilibrated 5.5. ×10 cm. column packed with XAD-II resin. The column is then washed with water and eluted with methanol. The methanol eluate is dried and evaporated affording 750 mg. of residue. 600 Mg. of this residue is dissolved in 8 ml. of methanol and applied to 4 preparative layer chromatography plates coated with 500μ of silica gel $GF_{254}$. The plates are developed with 15% methanol in chloroform. The progress of the development is followed by observing the ultraviolet light fluorescence quenching band. This band is removed and eluted with 15% methanol in chloroform. The eluate is dried and evaporated to dryness affording 171 mg. of residue which is a mixture of $A_1$, $A_2$ and $B_1$ components.

EXAMPLE 3

900 Ml. of fermentation broth as prepared in Example 1 is combined with 900 ml. of acetone and shaken and filtered through a bed of diatomaceous earth filtering aid. The filtrate is evaporated to remove the organic solvent and the aqueous residue is passed through a column of XAD-II resin in a 6 by 15.5 cm. column. The column is washed with water and eluted with 600 ml. of methanol. The methanol eluate is evaporated to dryness in vacuo and the residue dissolved in 10 ml. of methanol. This solution is placed on 6 preparative layer chromatography plates with a 2 mm. layer of silica gel $GF_{254}$. The plates are developed with chloroform containing 17% methanol. The plates are examined with an ultraviolet light and those bands where ultraviolet fluorescence is quenched are collected and eluted from the silica gel with 12% methanol in chloroform. The eluate is evaporated to dryness in vacuo. 121.8 Mg. of the material removed from the preparative layer chromatography plates is dissolved in 2 ml. of methylene chloride and placed on 10 prewashed silica gel preparative layer chromatography plates with a 500μ coating of silica gel $HF_{254}$. The plates are developed continuously for 20 hours in methylene chloride containing 10% methanol and 1% concentrated ammonium hydroxide. Non-acidic components, including $B_1$, of the mixture accumulate in the solvent front. The major components, $A_1$ having the lowest Rf and $A_2$ with a slightly higher Rf, completely separated under these conditions. The respective bands containing $A_1$ and $A_2$ are removed from the plates and eluted with chloroform containing 10% methanol. The eluates are filtered, evaporated, redissolved in methylene chloride, filtered, diluted with benzene and lyophilized affording 76.9 mg. of $A_1$ and 7.7 mg. of $A_2$.

EXAMPLE 4

133 Mg. of an enriched mixture of $A_1$, $A_2$ and $B_1$ compounds as prepared in Example 2 are dissolved in a minimum amount of methylene chloride and chromatographed on 4 prewashed plates with a 500μ coating of silica gel $HF_{254}$, developing with methylene chloride containing 6% methanol and 1% concentrated ammonium hydroxide. This is followed by methylene chloride containing 10% methanol and 1% concentrated ammonium hydroxide. The band containing the $A_1$ component is observed under ultraviolet light and removed from the plates, dissolved in methylene chloride containing 10% methanol followed by elution with methanol alone. The eluate is evaporated to dryness in vacuo, and the residue dissolved in methylene chloride, filtered, diluted with benzene and lyophilized affording 59 mg. of $A_1$.

EXAMPLE 5

270 Mg. of a mixture of $A_1$, $A_2$ and $B_1$ as prepared in Example 2 is dissolved in 3 ml. of methylene chloride and chromatographed on 9 prewashed preparative layer chromatography plates with a 250μ coating of silica gel $HF_{254}$, and developed 3 times with chloroform containing 20% methanol and 2% concentrated ammonium hydroxide. Under these conditions components moving faster than $A_1$ and $A_2$ separated into several bands which are individually recovered. The major band of this mixture with the second highest Rf affords 41 mg., after separation from the plates and lyophilization as in Examples 3 and 4, of componenet $B_1$.

EXAMPLE 6

Using nuclear magnetic resonance, mass spectroscopy and other analytical techniques, the structures of components $A_1$, $A_2$ and $B_1$, as elaborated above, have been determined. Some of the characteristic spectral data are set forth below.

| | |
|---|---|
| $A_1$ | Molecular Formula $C_{39}H_{60}O_{12}$ Molecular weight 720 Mass spectrometry: $M^+$ not observed, characteristic fragment ions found at m/e 586.3861, $C_{35}H_{54}O_7$, calc. 586.3855 ($M^+$ - water and fumaric acid); 568.3809, $C_{35}H_{52}O_6$, calc. 568.3750 (586-water); 525.3176, $C_{32}H_{45}O_6$, calc. 525.3204 (568-$C_3H_7$) Ultraviolet spectroscopy: λ max (methanol) 210 nm (ε 26,300), 245 nm (ε 35,590) and 284.5 nm (ε 15,880). |
| $A_2$ | Molecular Formula $C_{40}H_{62}O_{12}$ Molecular weight 734 Mass spectrometry: $M^+$ observed m/e 734, characteristic fragment ions found at m/e 586 ($M^+$ - methanol and fumaric acid), 568 (586-water), 525 (568-$C_3H_7$) Ultraviolet spectroscopy: λ max (methanol) 209 nm (ε 24,170), 246 nm (ε 32,870) and 283 nm (ε 14,120). |
| $B_1$ | Molecular Formula $C_{36}H_{60}O_9$ Molecular weight 636 Mass spectrometry: $M^+$ not observed, characteristic fragmentations found at m/e 618 ($M^+$ - water), m/e 600 ($M^+$ - 2 water), m/e 586 ($M^+$ - water and methanol), m/e 568 (586-water) and m/e 525 (568-$C_3H_7$). Ultraviolet spectroscopy: λ max (methanol) 246 nm (ε 38,200) and 284.5 nm (ε 16,950). |

What is claimed is:

1. A compound having the formula:

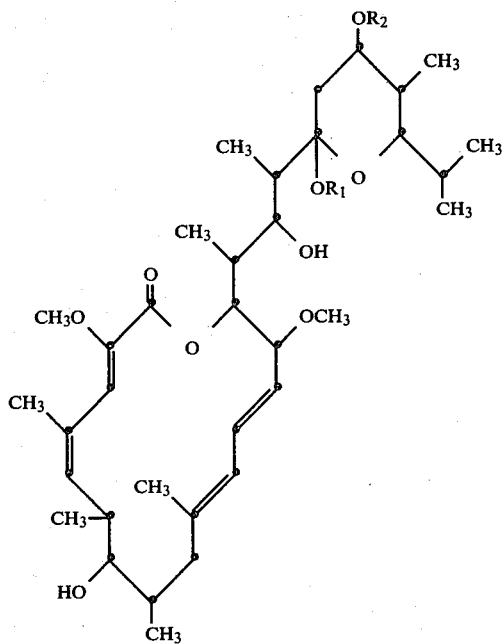

wherein the variables $R_1$ and $R_2$ have the following meanings for the compounds identified as $A_1$, $A_2$ and $B_1$:

| Compound | $R_1$ | $R_2$ |
|---|---|---|
| $A_1$ | H | —CO—CH=CH—COOH |
| $A_2$ | —CH$_3$ | —CO—CH=CH—COOH |
| $B_1$ | H | —CH$_3$ |

2. The compound of claim 1 which is compound $A_1$.

3. The compound of claim 1 which is compound $A_2$.

4. The compound of claim 1 which is compound $B_1$.

5. A composition useful for the prevention and treatment of parasite infections which comprises an inert carrier having an effective antiparasitic amount of one, two or three of the compounds of claim 1 incorporated therein.

6. A method for the prevention and treatment of parasite infections which comprises administering to an animal infected with parasites, an effective amount of a compound of claim 1.

7. A composition useful for the prevention and treatment of agricultural pest infestations which comprises an inert carrier having an effective pesticidal amount of one, two or three of the compounds of claim 1 incorporated therein.

8. A method for the prevention and treatment of agricultural pest infestations which comprises applying to an area infested with such pests an effective amount of a compound of claim 1.

9. A composition useful for the prevention and treatment of tapeworm infections which comprises an inert carrier having an effective antitapeworm amount of one, two or three of the compounds of claim 1 incorporated therein.

10. A method for the prevention and treatment of tapeworm infections which comprises administering to an animal infected with tapeworms an effective amount of a compound of claim 1.

* * * * *